(12) United States Patent
Lee et al.

(10) Patent No.: US 9,638,659 B2
(45) Date of Patent: May 2, 2017

(54) NANOWIRE FIELD-EFFECT SENSOR INCLUDING NANOWIRES HAVING NETWORK STRUCTURE AND FABRICATION METHOD THEREOF

(71) Applicant: POSTECH ACADEMY-INDUSTRY FOUNDATION, Pohang-si, Gyeongsangbuk-do (KR)

(72) Inventors: Jeong Soo Lee, Pohang-si (KR); Chan Oh Park, Pohang-si (KR); Dong Hoon Kim, Busan-si (KR); Ki Hyun Kim, Woolsan-si (KR)

(73) Assignee: POSTECH ACADEMY-INDUSTRY FOUNDATION, Pohang-si, Gyeongsangbuk-Do (KR)

( * ) Notice: Subject to any disclaimer, the term of this patent is extended or adjusted under 35 U.S.C. 154(b) by 0 days.

(21) Appl. No.: 15/053,109

(22) Filed: Feb. 25, 2016

(65) Prior Publication Data

US 2016/0252478 A1 Sep. 1, 2016

(30) Foreign Application Priority Data

Feb. 26, 2015 (KR) ........................ 10-2015-0027608

(51) Int. Cl.
*G01N 27/414* (2006.01)
*H01L 21/265* (2006.01)
(Continued)

(52) U.S. Cl.
CPC ... *G01N 27/4146* (2013.01); *H01L 21/26513* (2013.01); *H01L 29/0649* (2013.01);
(Continued)

(58) Field of Classification Search
CPC ......... B82Y 10/00; B82Y 15/00; B82Y 30/00; G01N 27/4145; G01N 27/4146; H01L 29/0673; H01L 29/0665
(Continued)

(56) References Cited

U.S. PATENT DOCUMENTS

| | | | |
|---|---|---|---|
| 6,870,235 B2 * | 3/2005 | Abstreiter | G01N 27/4145 257/17 |
| 7,893,466 B2 * | 2/2011 | Yang | G01N 27/4145 257/253 |

(Continued)

FOREIGN PATENT DOCUMENTS

| | | |
|---|---|---|
| KR | 10-2012-0117231 | 10/2012 |
| KR | 10-1220285 | 1/2013 |

*Primary Examiner* — David Vu
*Assistant Examiner* — Jonathan Han
(74) *Attorney, Agent, or Firm* — Kile Park Reed & Houtteman PLLC

(57) ABSTRACT

Disclosed herein is a technology for fabricating a nanowire field-effect sensor, in which a bulk silicon substrate is used so that the fabrication cost of the sensor can be reduced while the integration density of the sensor can be increased. In addition, the nanowire field-effect sensor includes a nano-network having a network structure in which pins are vertically arranged on the sidewalls of the network, respectively, and a gate insulating layer is applied to the pins. Due to this nano-network, the detection area of the sensor can be increased to increase its sensitivity, and the structural stability of the sensor can be ensured.

10 Claims, 25 Drawing Sheets

(51) Int. Cl.
*H01L 29/06* (2006.01)
*H01L 29/423* (2006.01)

(52) U.S. Cl.
CPC .... *H01L 29/0673* (2013.01); *H01L 29/42356* (2013.01); *H01L 29/42364* (2013.01)

(58) Field of Classification Search
USPC .......... 257/253, 414, 9, 20; 438/49, 22, 962
See application file for complete search history.

(56) References Cited

U.S. PATENT DOCUMENTS

| | | | | |
|---|---|---|---|---|
| 2006/0228723 | A1* | 10/2006 | Bradley | B01L 3/50857 435/6.11 |
| 2007/0132043 | A1* | 6/2007 | Bradley | B82Y 10/00 257/414 |
| 2008/0274912 | A1* | 11/2008 | Johnson | B82Y 30/00 506/13 |
| 2010/0283031 | A1* | 11/2010 | Kim | G01N 33/5432 257/9 |
| 2012/0214172 | A1* | 8/2012 | Chen | B82Y 15/00 435/6.19 |
| 2014/0363821 | A1* | 12/2014 | Bashir | H05B 6/802 435/6.12 |

* cited by examiner

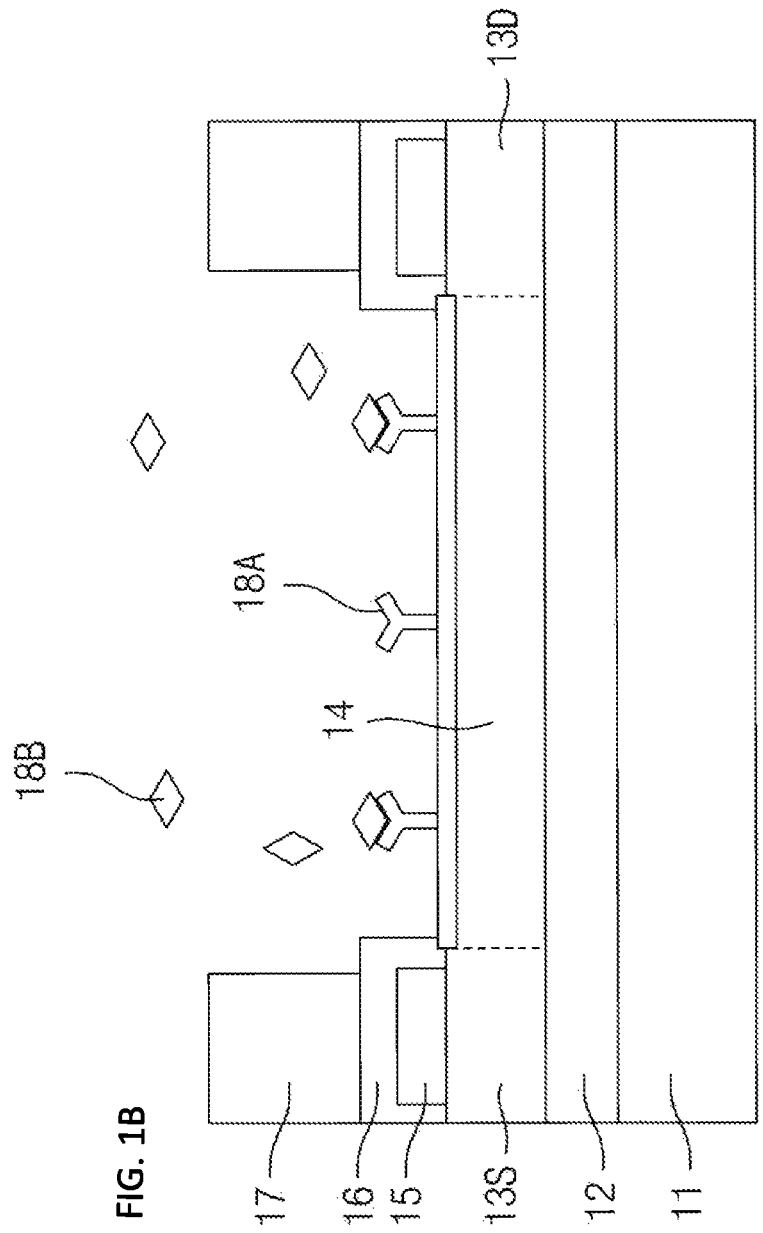

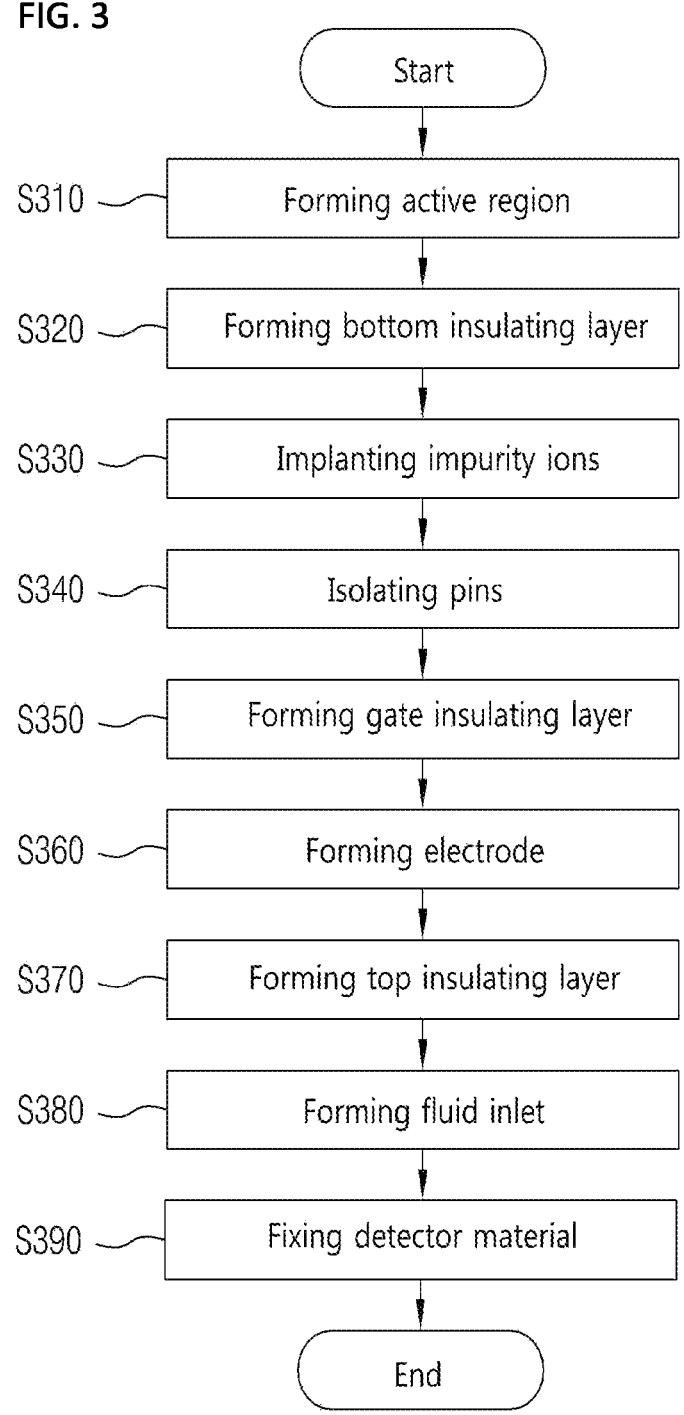

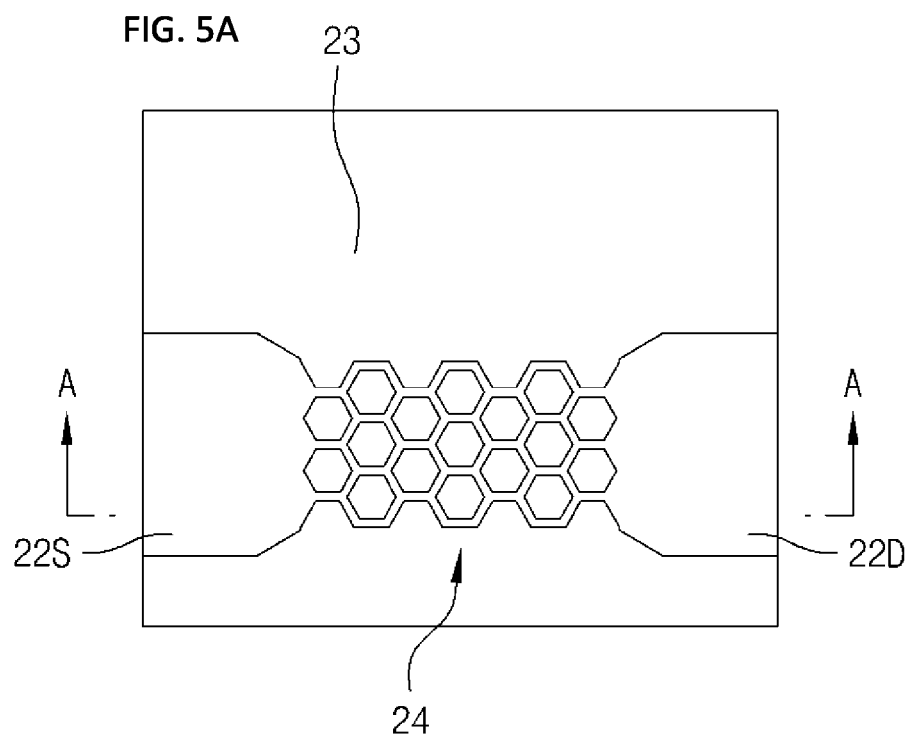

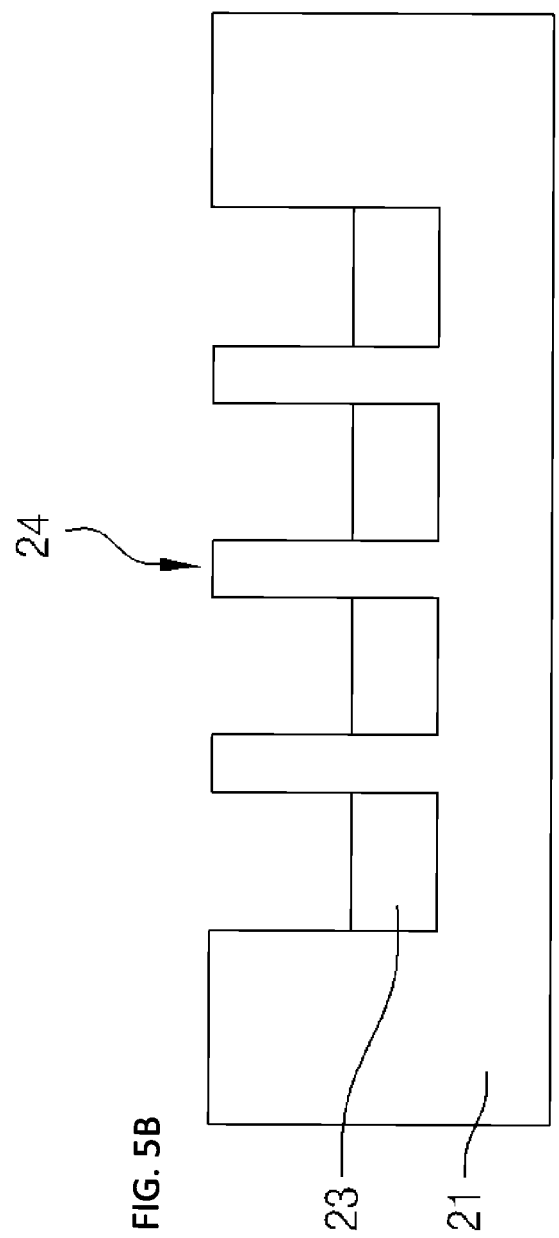

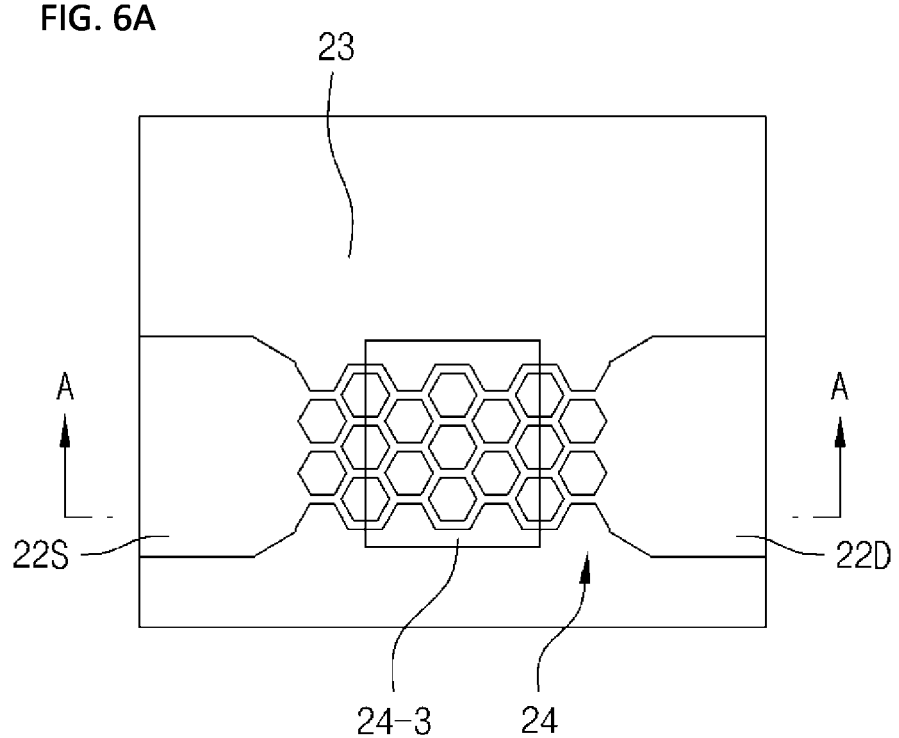

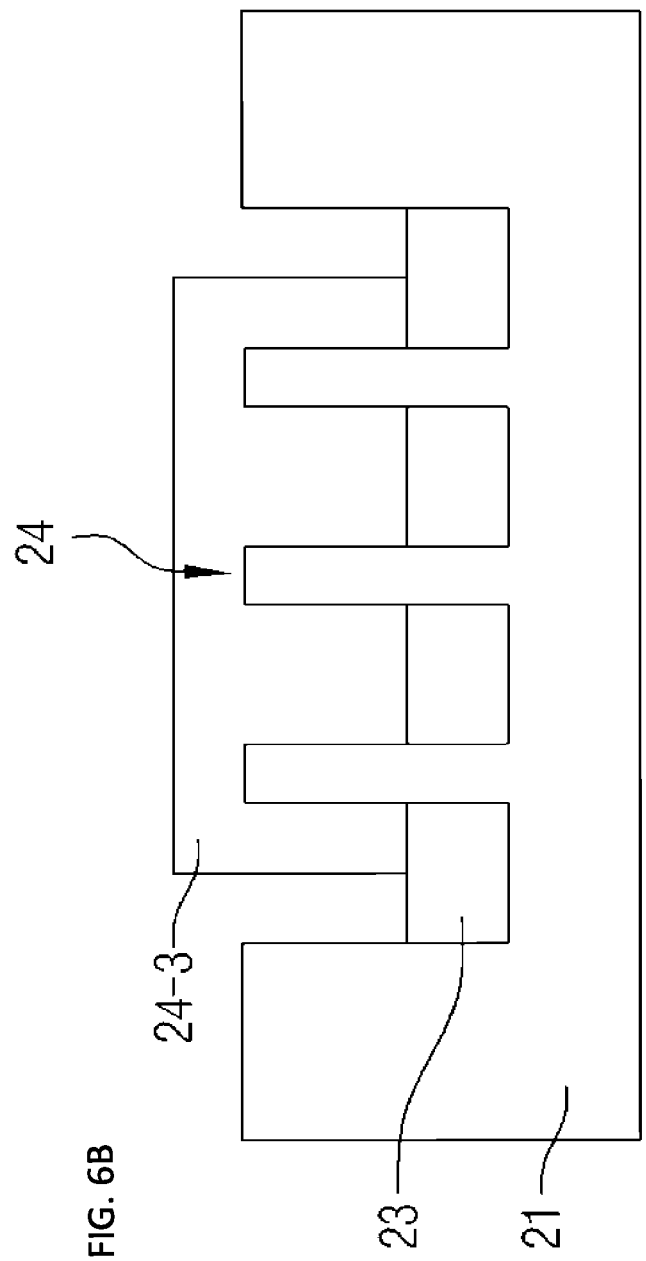

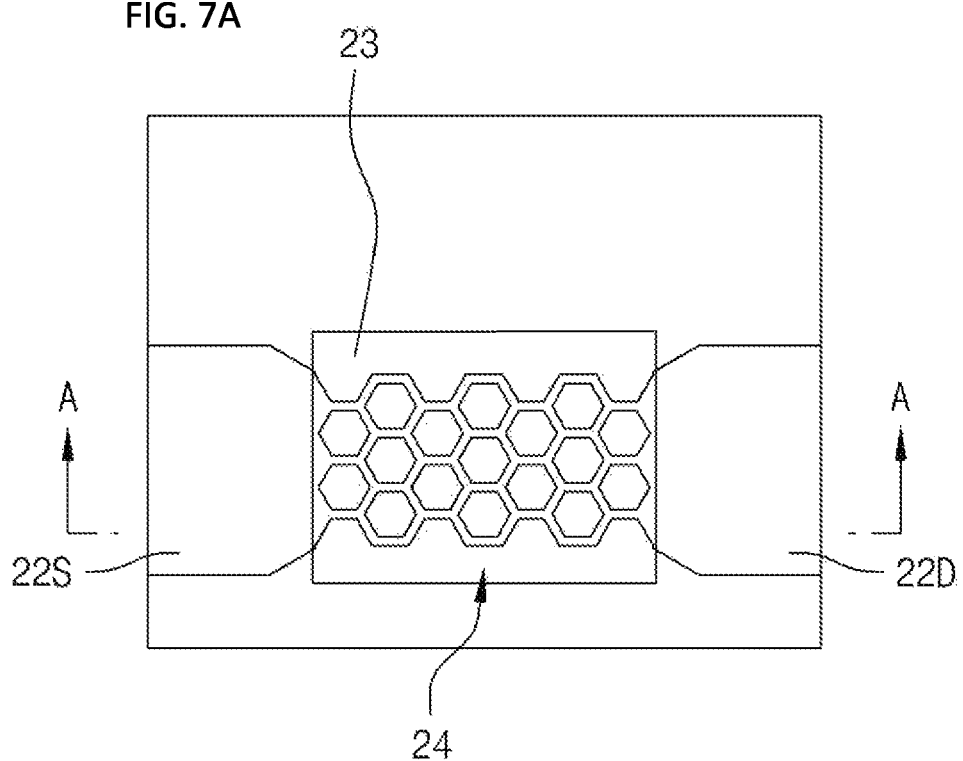

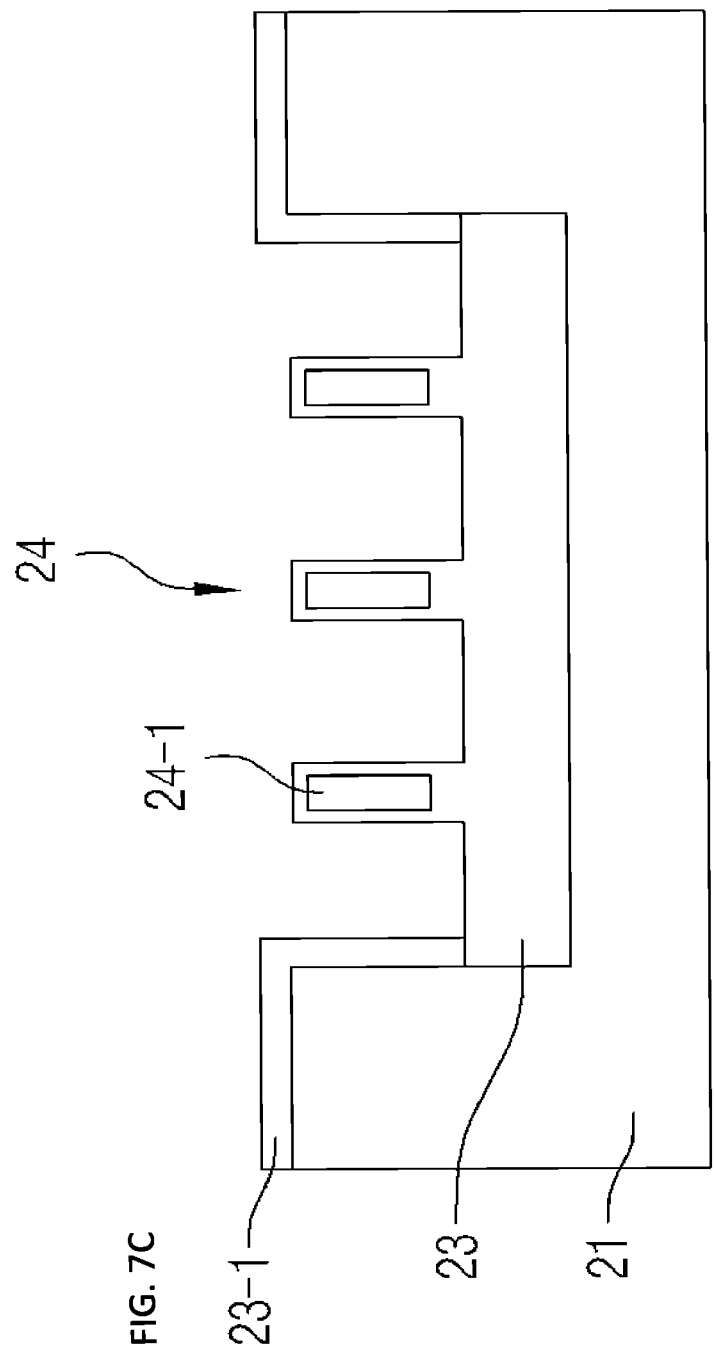

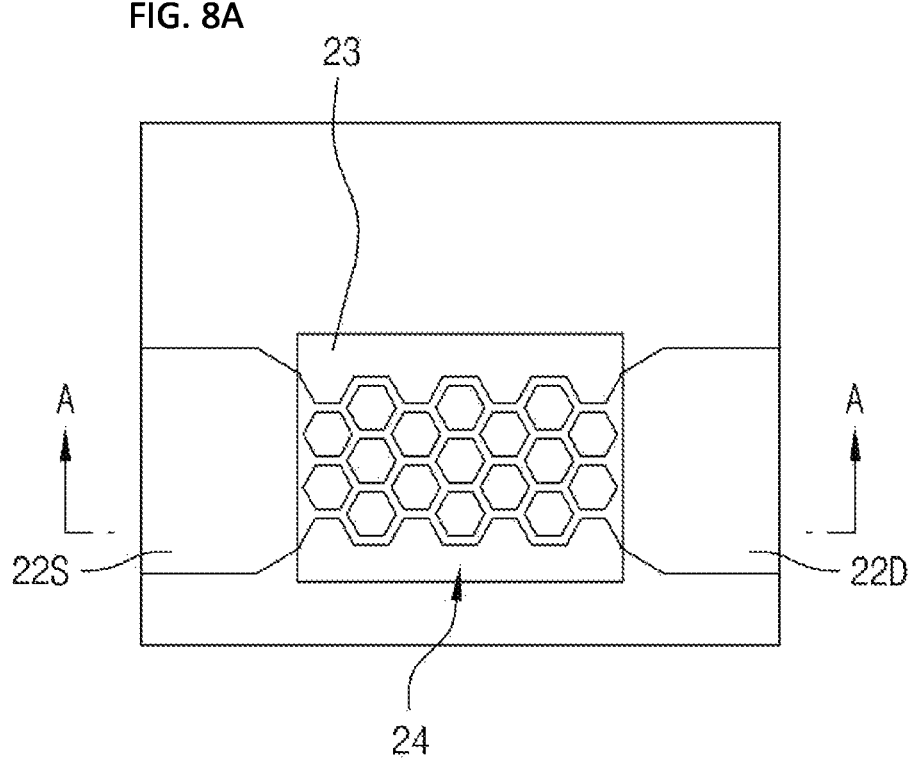

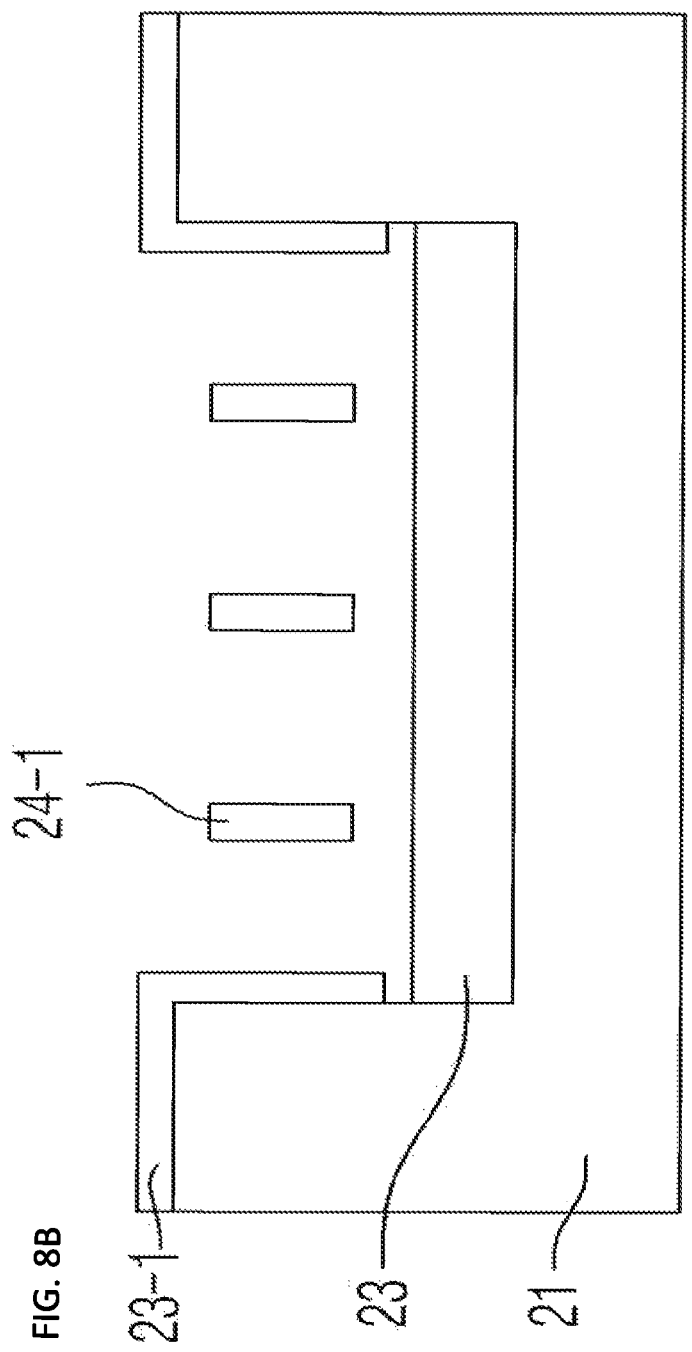

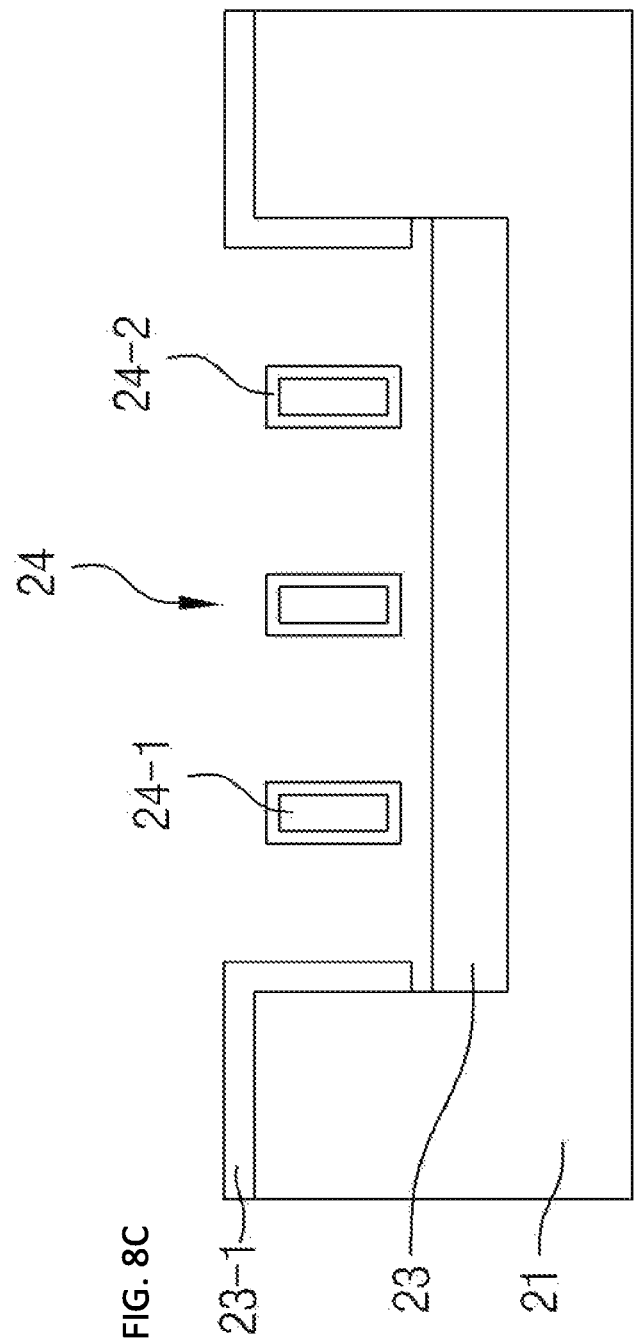

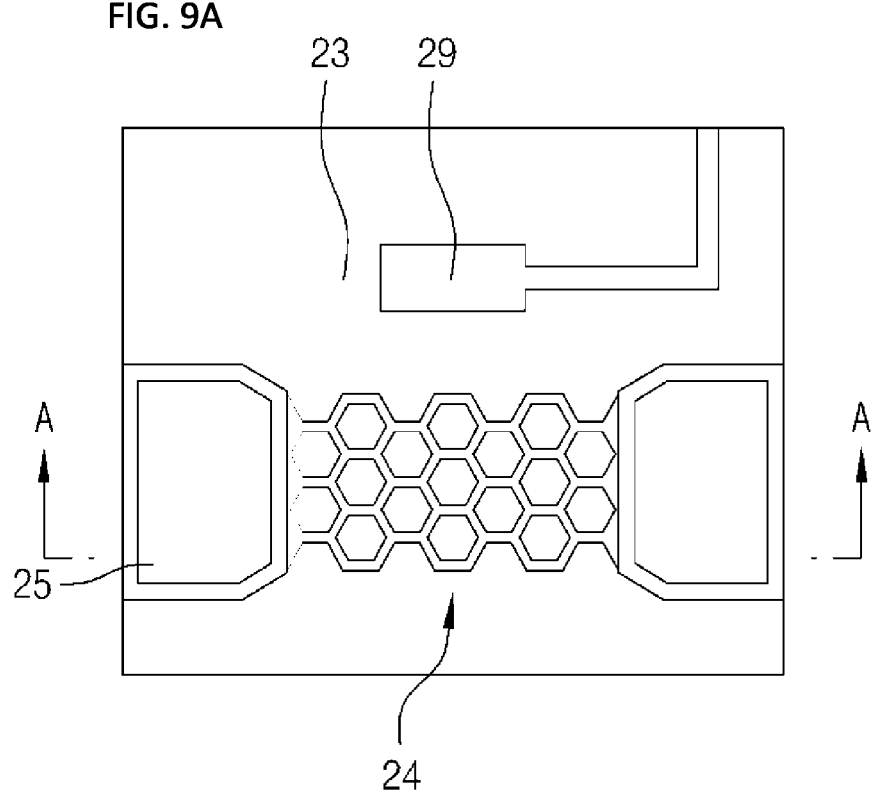

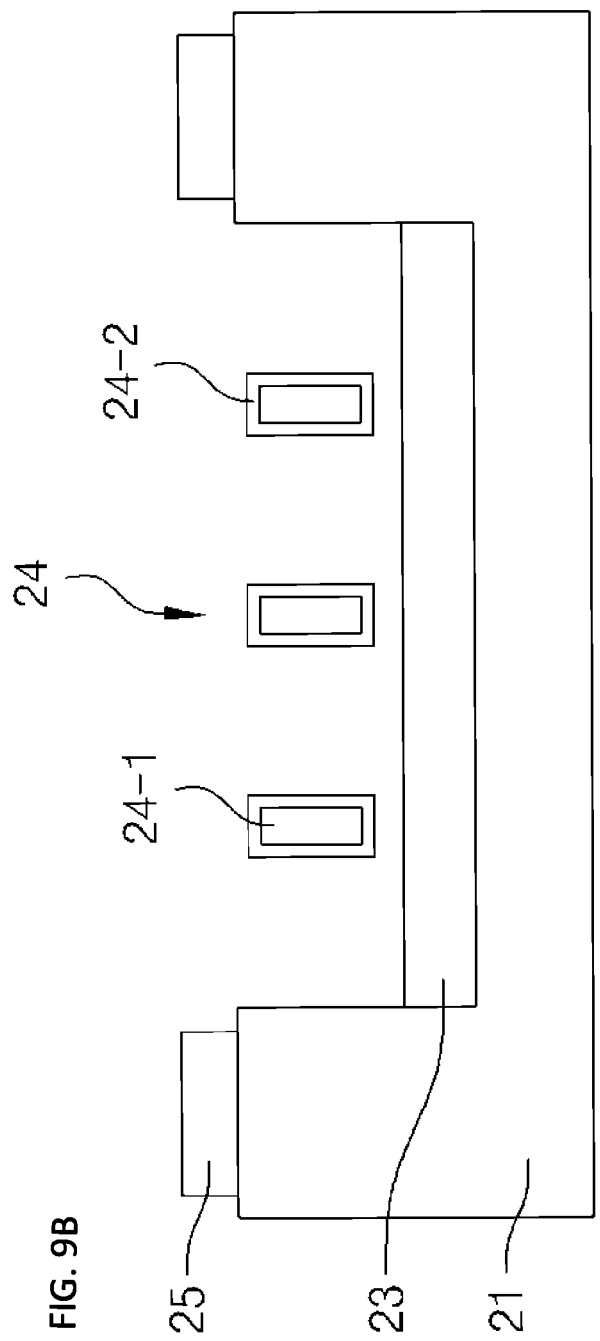

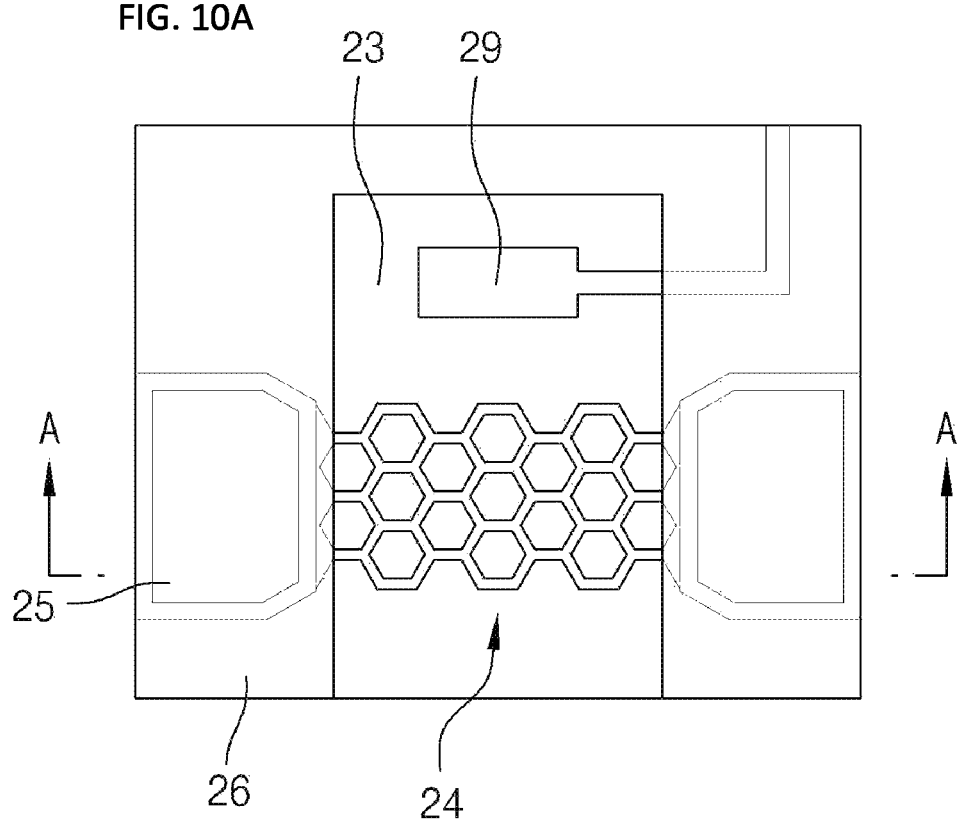

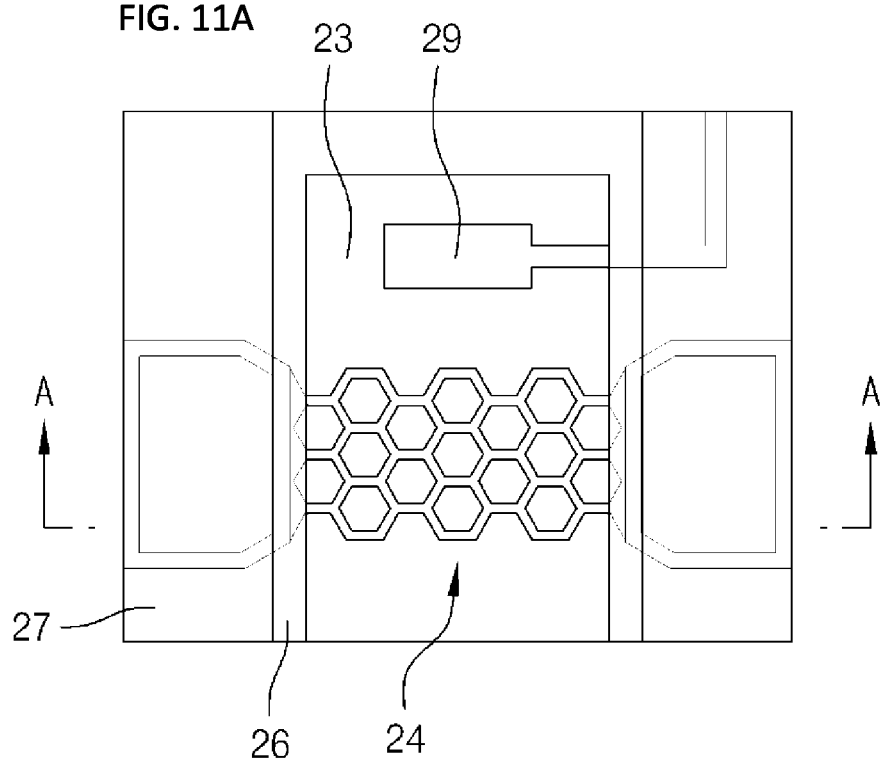

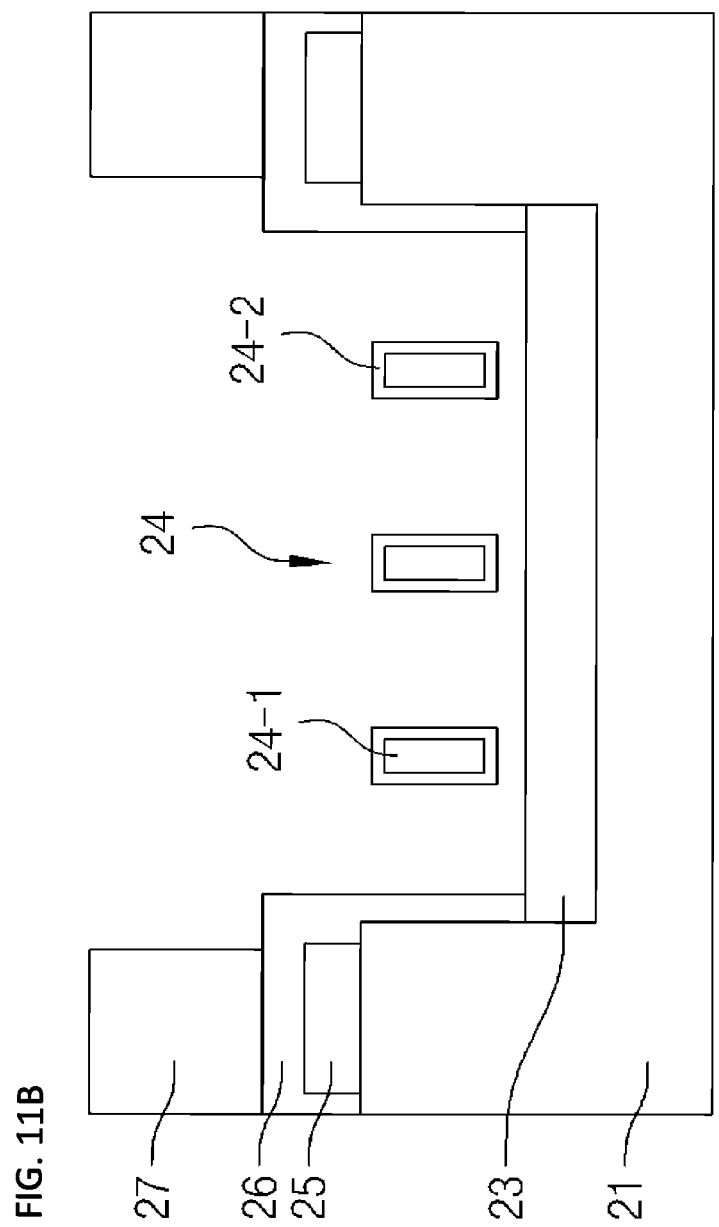

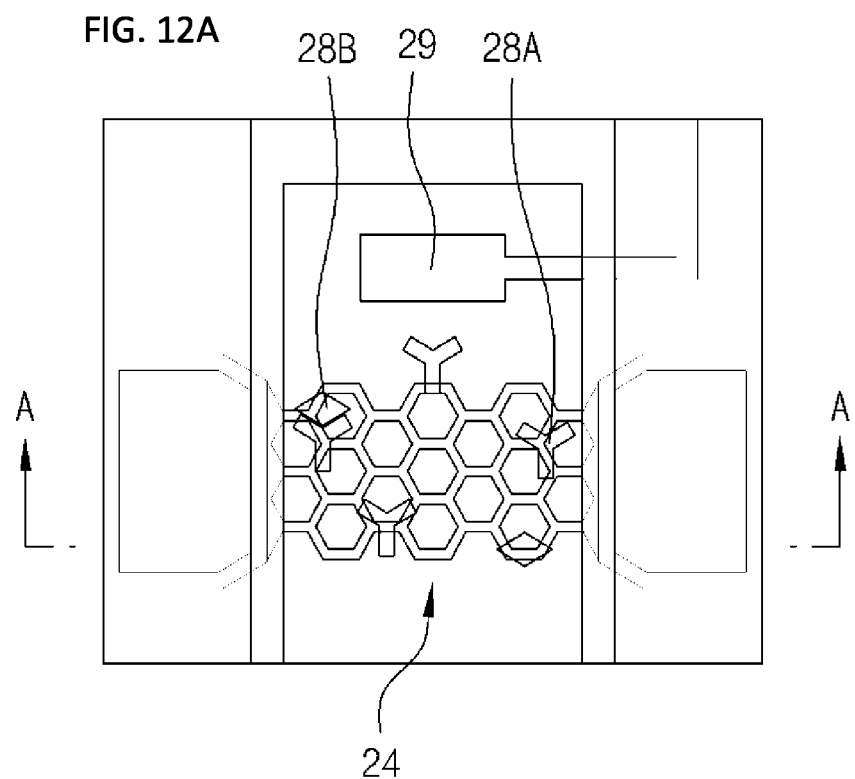

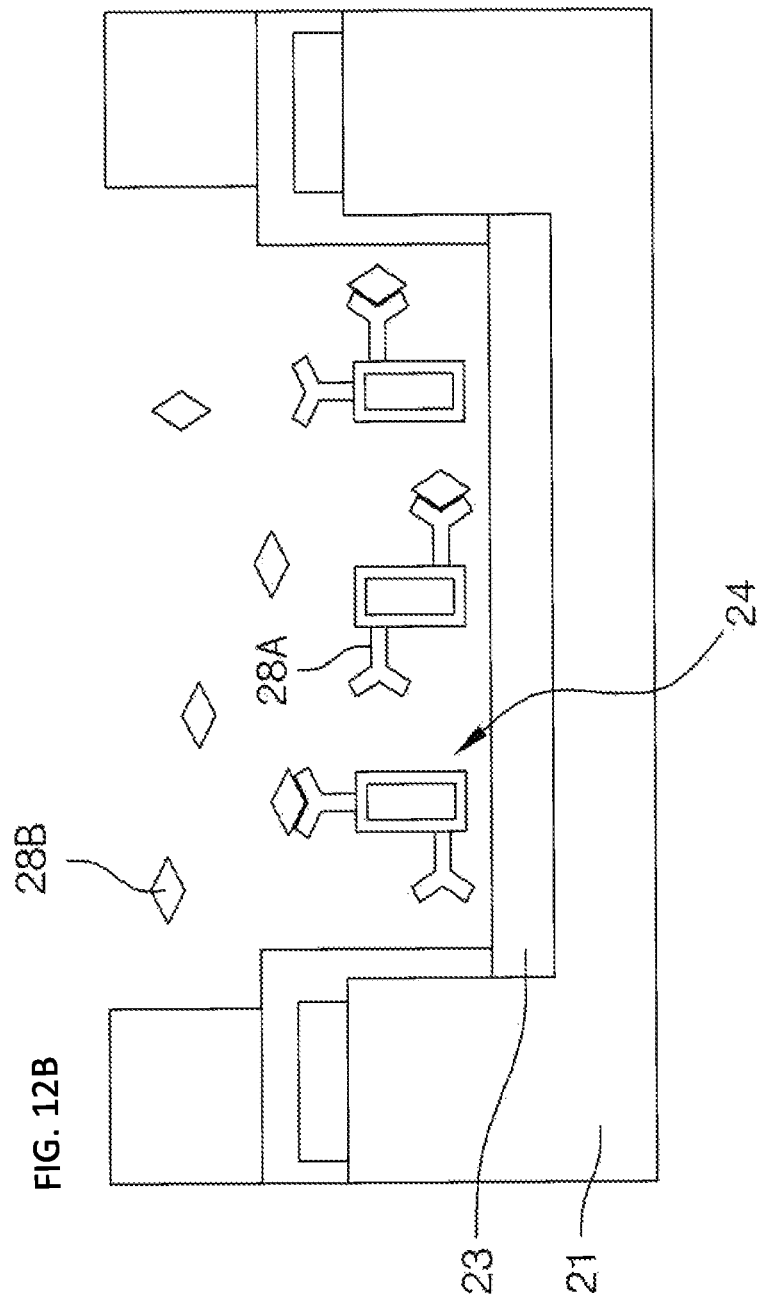

NANOWIRE FIELD-EFFECT SENSOR INCLUDING NANOWIRES HAVING NETWORK STRUCTURE AND FABRICATION METHOD THEREOF

BACKGROUND OF THE INVENTION

Field of the Invention

The present invention relates to a technology for fabricating a nanowire field-effect sensor, and more particularly, to a nanowire field-effect sensor including nanowires having a network structure and to a fabrication method, in which a bulk silicon substrate is used so that the fabrication cost of the sensor can be reduced and the integration density of the sensor can be increased, and a nano-network is effectively insulated so that the high sensitivity and structural stability of the sensor can be ensured.

Description of the Prior Art

An electrochemical sensor is a device that converts a physical or biochemical signal from a target material to be detected into an electrical signal, and is characterized by having a small size and a high detection speed, compared to conventional fluorescent sensors. Such electrochemical sensors are expected to be widely used in applications, including biosensors, chemical sensors and environmental sensors, depending on the kind of target material.

The electrochemical sensor includes a receptor material that selectively reacts with a target material, a buffer solution and a submerged gate electrode, and is operated in a solution, unlike a field effect transistor that is an electronic element. For this reason, it is important to minimize current leakage from the electrochemical sensor. In the electrochemical sensor, a detector material that selectively binds to a target material in order to detect the target material is fixed to the detection surface of the sensor through a series of chemical treatments. When the charged target material reacts with and binds to the receptor material on the detection surface, the electrical conductivity in the channel of the sensor is changed by the charge of the target material, and the target material can be detected by observing this change in the electrical conductivity of the sensor. The target material bound to the receptor material fixed to the detection surface by a chemical reaction is not easy to separate, and the fixed receptor material is difficult to reuse after its separation from the detection surface. In addition, if the sensor is continuously used, the characteristics of the sensor, such as sensitivity, will be deteriorated. For this reason, a sensor for application to a product should be used in a disposable manner without being reused. To commercialize an electrochemical sensor as a product, cost effectiveness and the ease of integration are important, in addition to characteristics such as high sensitivity, high specificity and fast response-time.

Among electrochemical sensors, a field-effect sensor with nanowires is attracting attention due to its high sensitivity and selectivity and fast response time. The nanowire structure has excellent gate control ability due to its high area-to-volume ratio, and for this reason, shows a great change in electrical conductivity even when the change in the charge of a target material by the detection surface is small, indicating that the nanowire structure shows high sensitivity. In addition, because the field-effect sensor can detect a target material in real time by an electrical measurement method, it can be produced in large amounts using existing CMOS semiconductor process technology.

FIG. 1A illustrates the structure of a nanowire field-effect transistor including a silicon-on-insulator (SOI) substrate according to the prior art, and FIG. 1B is a cross-sectional view taken along line A-A of FIG. 1A.

Referring to FIGS. 1A and 1B, an SOI substrate 11 and a bottom insulating layer 12 are sequentially deposited, and then a source electrode region 13S and a drain electrode region 13D are formed on both sides of the bottom insulating layer 12 so as to be opposite to each other, and nanowires 14 having a gate insulating layer applied thereto are connected between the two electrode regions 13S and 13D.

A detector material 18A is attached to the nanowires 14, and a target material 18B is selectively attached to the detector material 18A. In this case, the electrical conductivity of the nanowire channel region is changed by the charge of the target material 18B, and the nanowire field-effect sensor detects this change in the electrical conductivity and outputs the result of detection. Herein, the electric potential of a solution that is filled in the nanowire channel region can be fixed using a separate submerged gate electrode 19.

The nanowire field-effect sensor according to the prior art as described above uses an SOI wafer as a substrate, and has a structure in which the top silicon layer is completely isolated from the substrate by the bottom insulating layer. To form the one-dimensional nanowires as described above, an element is fabricated on the expensive SOI substrate, and for this reason, the nanowire field-effect sensor has a problem in that it is costly. For reference, the price of an SOI substrate having a thin top silicon layer, which is used to form nanowires, is at least 20 times higher than the price of a bulk silicon substrate. In addition, because it is impossible to reuse a receptor material and a target material, which are used for detection in the nanowire field-effect sensor that is a biosensor, the nanowire field-effect sensor according to the prior art has a problem in that many maintenance costs are incurred.

Furthermore, in the case in which nanowires equal or similar to those used in the nanowire field-effect sensor according to the prior art are used, the sensitivity of the sensor itself is very high, but there is a shortcoming in that the area of the nanowire is very small (several square nanometers to several square microns), and thus the amount of target material that is transferred from the buffer solution to the detection surface is necessarily very limited, indicating that the sensor has low sensitivity.

In addition, in the case of the nanowire field-effect sensor according to the prior art, the nanowires to which the detector material is fixed can be formed by a bottom-up or top-down method. In the case of the bottom-up method, nanowires formed using a semiconductor processing technique such as CVD (chemical vapor deposition) are arranged at specific positions to thereby fabricate a sensor, and thus the synthesis and arrangement of the nanowires are not easy, making it difficult to produce the sensor in large amounts.

SUMMARY OF THE INVENTION

It is an object of the present invention to provide a nanowire field-effect sensor and a fabrication method thereof, in which a bulk silicon substrate is used so that the fabrication cost of the sensor is reduced while the integration density thereof is increased, and a nano-network is effectively insulated, and the sensor includes nanowires having a network structure in which pins are vertically arranged on the sidewalls of the network, respectively.

To achieve the above object, in accordance with an embodiment of the present invention, there is provided a nanowire field-effect sensor including nanowires having a network structure, the nanowire field-effect sensor including: a source electrode region and drain electrode region formed on both sides of a bulk silicon substrate so as to be opposite to each other; a nano-network having a network structure and connected between the source electrode region and the drain electrode region; a bottom insulating layer formed between the bulk silicon substrate and the nano-network in such a manner that the bottom portion of each of the source electrode region and the drain electrode region is maintained connected to the bulk silicon substrate and the bottom portion of the nano-network is completely insulated from the bulk silicon substrate; and a detector material fixed to the nano-network so as to selectively react with a target material that is externally introduced.

In accordance with another embodiment of the present invention, there is provided a method for fabricating a nanowire field-effect sensor including nanowires having a network structure, the method including the steps of: forming on a bulk silicon substrate an active region, which includes a nano-network, a source electrode region and a drain electrode region, by a lithography process and an etching process; forming a bottom insulating layer for insulating between the active region and the bulk silicon substrate, in a region between the sidewalls of the nano-network, which excludes the active region, in such a manner that the bottom portion of each of the source electrode region and the drain electrode region is maintained connected to the bulk silicon substrate and the bottom portion of the nano-network is completely insulated from the bulk silicon substrate; implanting impurity ions into the source electrode region and the drain electrode region to increase the electrical conductivity of the source electrode region and the drain electrode region; forming a gate insulating layer on a pin vertically arranged on each sidewall of the nano-network in order to control the gate of the nanowire field-effect sensor; forming an electrode metal layer on the source electrode region and the drain electrode region, and forming a submerged gate electrode on the bulk silicon substrate in order to apply a gate potential to the nano-network; forming a top insulating layer on the electrode metal layer in order to prevent a current from leaking from the source electrode region and the drain electrode region through an electrolyte; forming a fluid inlet by forming a fluid channel layer for transferring a fluid to the nano-network and the submerged gate electrode; and fixing a detector material, which selectively reacts with a target material, to the surface of the nano-network.

BRIEF DESCRIPTION OF THE DRAWINGS

FIG. 1B is a cross-sectional view taken along line A-A of FIG. 1.

FIG. 3 is a flow diagram showing a method for fabricating a nanowire field-effect sensor according to another embodiment of the present invention.

FIG. 5A shows a step of forming a bottom insulating layer in a nanowire field-effect sensor according to the present invention.

FIG. 5B is a cross-sectional view taken along line A-A of FIG. 5A.

FIG. 6A shows a step of implanting impurity ions in a nanowire field-effect sensor according to the present invention.

FIG. 6B is a cross-sectional view taken along line A-A of FIG. 6A.

FIG. 7A shows a step of isolating pins in a nanowire field-effect sensor according to the present invention.

FIGS. 7B and 7C are cross-sectional views taken along line A-A of FIG. 7A.

FIG. 8A shows a step of forming a gate insulating layer in a nanowire field-effect sensor according to the present invention.

FIGS. 8B and 8C are cross-sectional views taken along line A-A of FIG. 8A.

FIG. 9A shows a step of forming an electrode in a nanowire field-effect sensor according to the present invention.

FIG. 9B is a cross-sectional view taken along line A-A of FIG. 9A.

FIG. 10A shows a step of forming a top insulating layer in a nanowire field-effect sensor according to the present invention.

FIG. 11A shows a step of forming a fluid inlet in a nanowire field-effect sensor according to the present invention.

FIG. 11B is a cross-sectional view taken along line A-A of FIG. 11A.

FIG. 12A shows a step of fixing a detector material in a nanowire field-effect sensor according to the present invention.

FIG. 12B is a cross-sectional view taken along line A-A of FIG. 12A.

DETAILED DESCRIPTION OF THE INVENTION

Hereinafter, preferred embodiments of the present invention will be described with reference to the accompanying drawings.

Figure 1A:
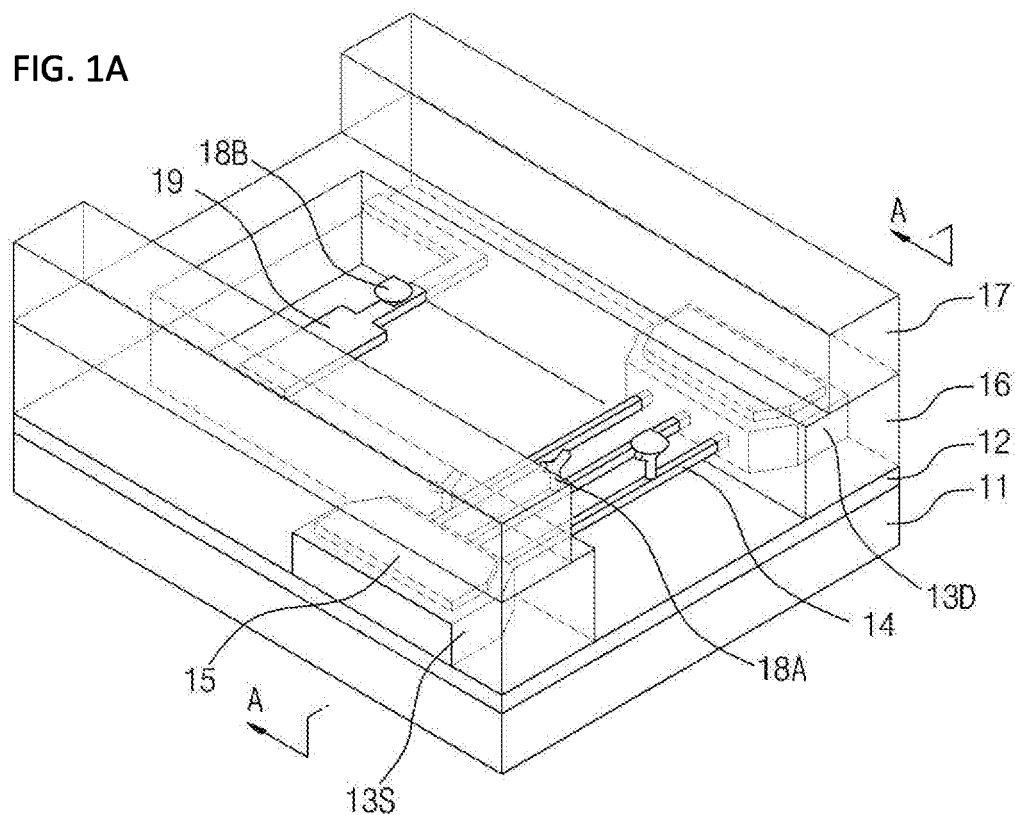
FIG. 1A illustrates the structure of a nanowire field-effect sensor including an SOI substrate according to the prior art.
Figure 2A:
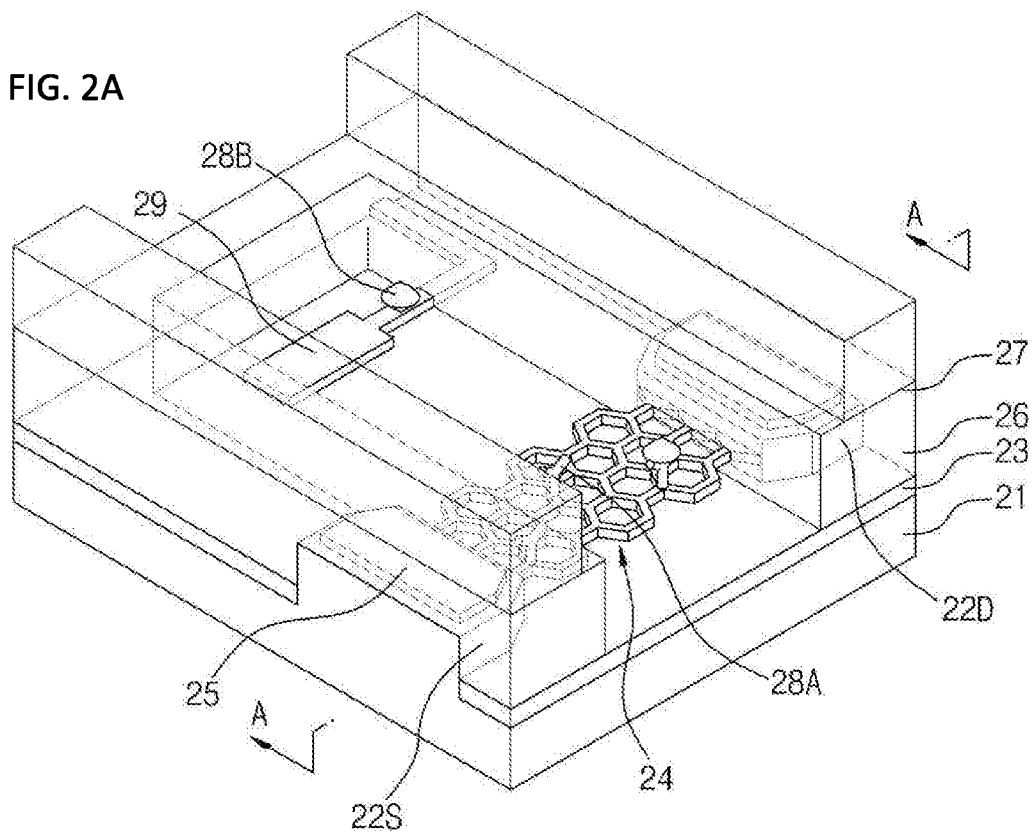
FIG. 2A illustrates the structure of a nanowire field-effect sensor according to an embodiment of the present invention.
Figure 2B:
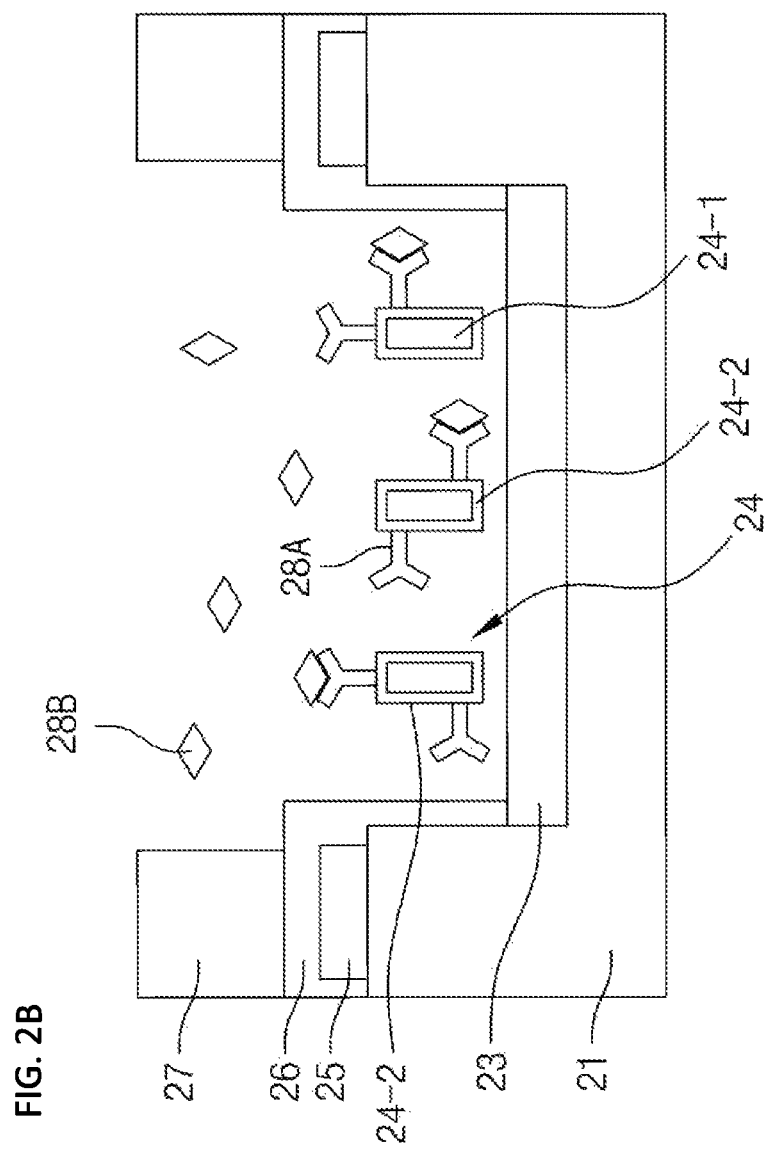
FIG. 2B is a cross-sectional view taken along line A-A of FIG. 2A.
Figure 4A:
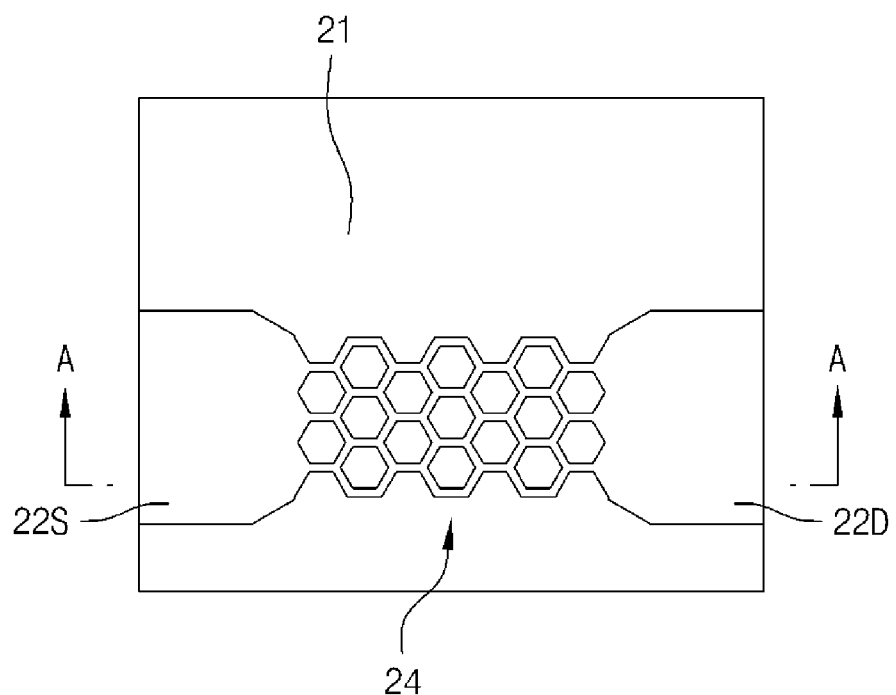
FIG. 4A shows a step of forming an active region in a nanowire field-effect sensor according to the present invention.
Figure 4B:
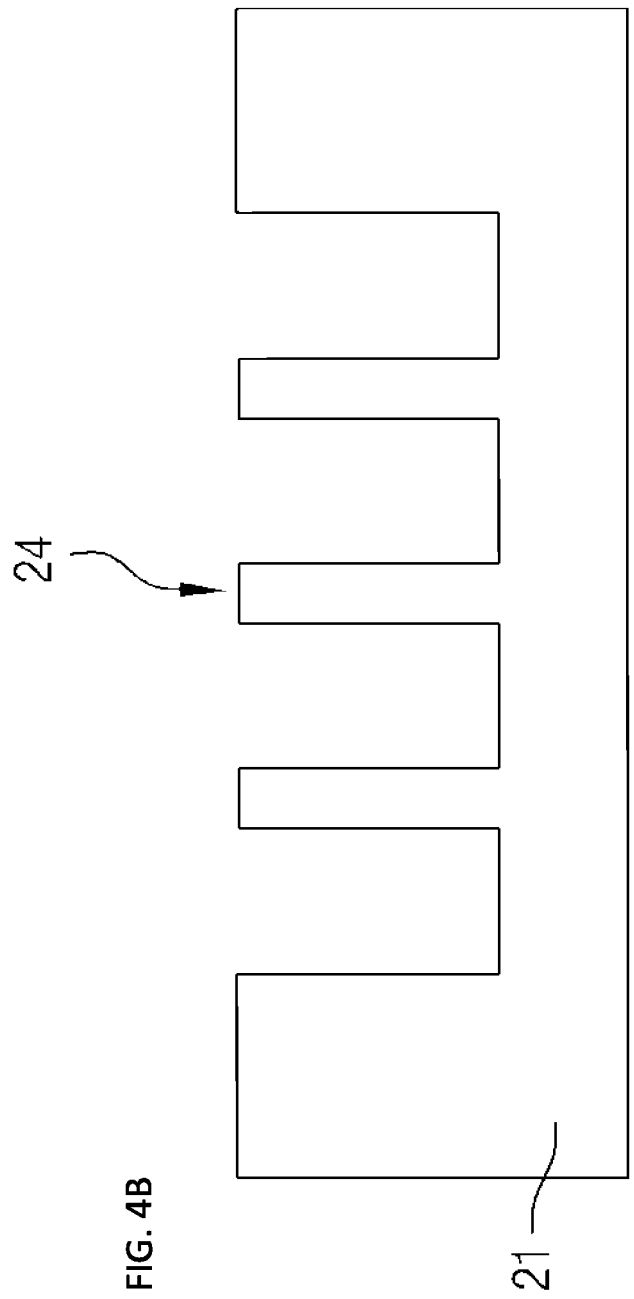
FIG. 4B is a cross-sectional view taken along line A-A of FIG. 4A.
Figure 7B:
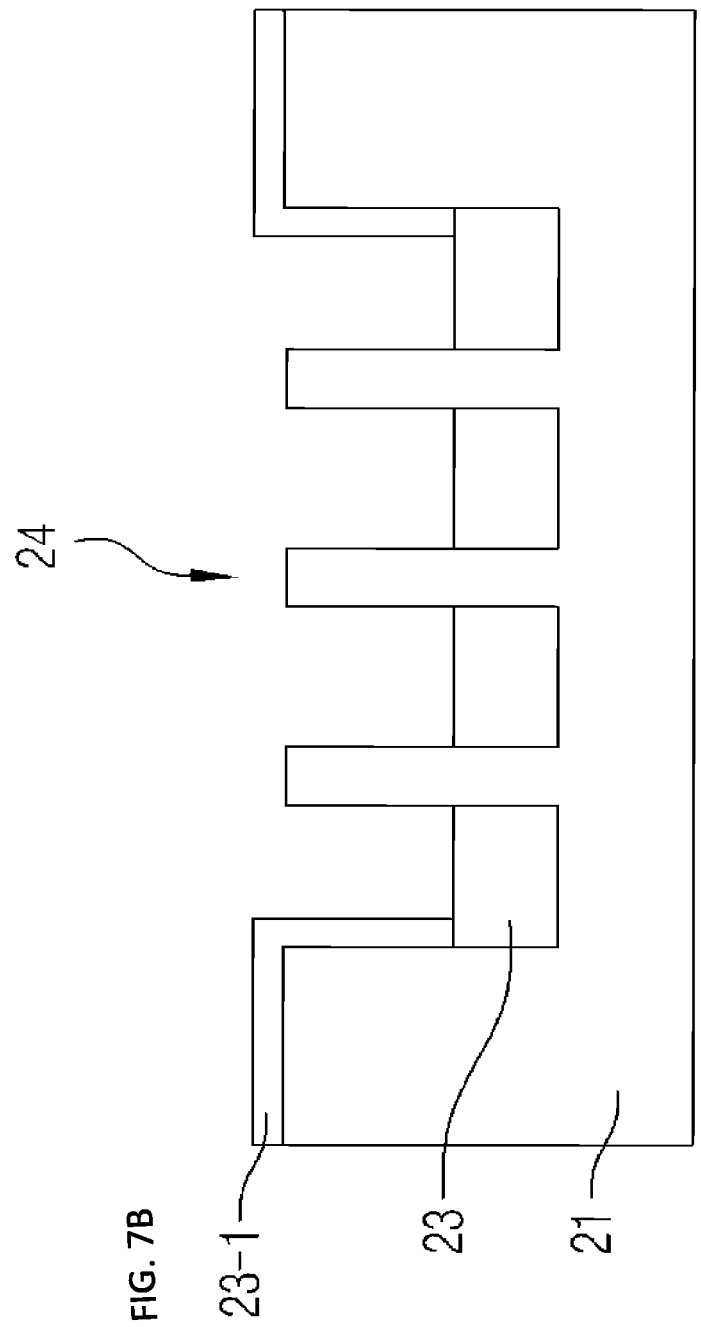
Figure 10B:
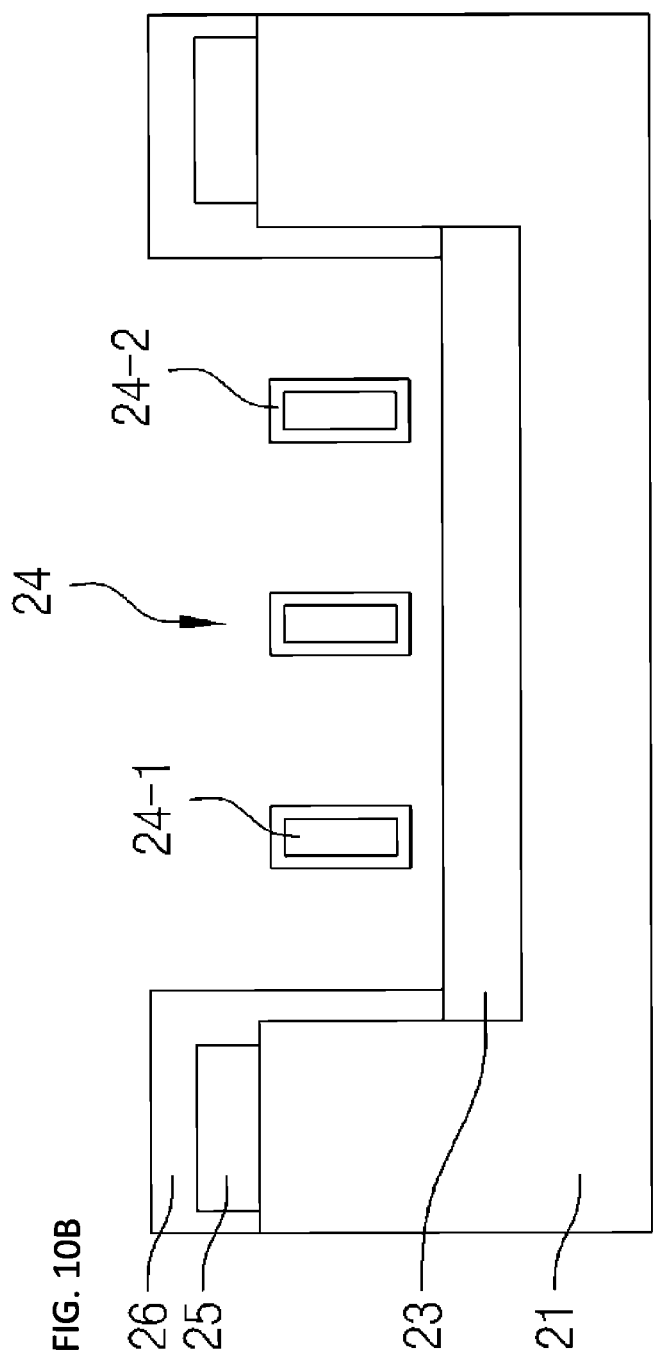
FIG. 10B is a cross-sectional view taken along line A-A of FIG. 10A.

FIG. 2A illustrates the structure of a nanowire field-effect sensor according to an embodiment of the present invention, and FIG. 2B is a cross-sectional view taken along line A-A of FIG. 2A.

Referring to FIGS. 2A and 2B, the nanowire field-effect sensor according to the embodiment of the present invention includes: a source electrode region 22S and drain electrode region 22D formed on both sides of a bulk silicon substrate 21 so as to be opposite to each other; a nano-network 24 connected between the source electrode region 22S and the drain electrode region 22D and having a network structure in which a gate insulating layer 24-2 is applied to a pin 24-1 arranged on each sidewall of the network; a bottom insulating layer 23 disposed between the bulk silicon substrate 21 and the nano-network 24 so as to insulate the nano-network 24 from the bulk silicon substrate; an electrode metal layer 25 deposited on each of the source electrode region 22S and the drain electrode region 22D; a top insulating layer 26 and top fluid channel layer 27 sequentially formed on the electrode metal layer 25; a detector material 28A attached to the nano-network 24; a target material 28B which is selectively attached to the detector material 28A; and a submerged gate electrode 29 configured to fix the electric potential of a solution that is filled in a nanowire channel region.

The bulk silicon substrate 21 is about 20 times cheaper than an SOI substrate applied to a conventional nanosensor, and thus can significantly reduce the fabrication cost of the nanowire field-effect sensor. In addition, because the nanowire field-effect sensor can be fabricated on a substrate such as a signal processing logic circuit that is fabricated on the bulk silicon substrate 21, integration of the nanowire field-effect sensor system is very superior to integration of a conventional nanowire field-effect sensor. The material of the bulk silicon substrate 21 is not specifically limited, but may include one or more of semiconductor, polymer and nonconductor materials.

The nano-network 24 has a network structure in which a pin 24-1 is vertically arranged on each sidewall and a gate insulating layer 24-2 is applied to the pin 24-1. As used herein, the term "network structure" means a structure in which shapes such as circular shapes and polygonal shapes (including hexagonal shapes) are continuously arranged in all directions. This embodiment illustrates that the nano-network 24 has a hexagonal structure, that is, a hexagonal lattice structure. The structure of the pin 24-1 is not specifically limited, but may include various structures such as a cylindrical structure or polygonal structures including a rectangular structure.

Thus, the nanowire field-effect sensor having the nano-network 24 can guarantee a high structural stability compared to a conventional nanowire field-effect sensor having a linear pin. In addition, the nano-network 24 having the above-described structure can increase the detection surface area of the nanowire field-effect sensor to increase the sensitivity of the sensor, and can prevent the characteristics of the sensor element from being deteriorated during a pin fabrication process.

The bottom insulating layer 23 is formed between the bulk silicon substrate 21 and the nano-network 24 by an oxidation process so as to insulate the nano-network 24 from the bulk silicon substrate 21. Accordingly, the lower end of each of the source electrode region 22S and the drain electrode region 22D is maintained in a state in which it is connected to the bulk silicon substrate 21, but the bottom portion of the nano-network 24 is completely isolated from the bulk silicon substrate 21. Therefore, the bottom insulating layer 23 enables insulation between the bulk silicon substrate 21 and the pins of the nano-network 24, and thus the amount of leakage current can be maintained at a level lower than the amount of leakage current that occurs when an SOI substrate is used, thereby preventing the sensor sensitivity from deteriorating.

The electrode metal layer 25 is deposited on each of the source electrode region 22S and the drain electrode region 22D, and the top insulating layer 26 and the top fluid channel layer 27 are sequentially deposited on the electrode metal layer 25.

The detector material 28A is attached to the nano-network 24 and serves to selectively bind to the target material 28B.

The submerged gate electrode 29 serves to fix the electric potential of a solution that is filled in the nanowire channel region.

Meanwhile, FIG. 3 is a flow diagram showing a method for fabricating a nanowire field-effect sensor according to another embodiment of the present invention. As shown therein, the method for fabricating the nanowire field-effect sensor includes the steps of: (S310) forming an active region; (S320) forming a bottom insulating layer; (S330) implanting impurity ions; (S340) isolating pins; (S350) forming a gate insulating layer; (S360) forming electrodes; (S370) forming a top insulating layer; (S380) forming a fluid inlet; and (S390) fixing a detector material.

A method for fabricating a nanowire field-effect sensor according to another embodiment of the present invention will now be described in detail with reference to FIGS. 4 to 12.

First, step (S310) of forming an active region is performed in which a source electrode region 22S, a drain electrode region 22D and a nano-network 24 are formed on a bulk silicon substrate. Step (S310) will now be described with reference to FIGS. 4A and 4B.

Using any one of electron beam lithography, stepper lithography and scanner lithography, a source electrode region 22S, a drain electrode region 22D and a nano-network 24 are patterned on a bulk silicon substrate 21. Then, an active region for the nanowire field-effect sensor is formed using a dry etching or wet etching process. The line width of the nano-network 24 is not specifically limited, but is preferably in the range from 5 nm, which is a process limitation, to 1 µm which is the maximum nanowire width that provides high sensitivity. The height of the nano-network 24 after etching is preferably in the range from 50 nm to 1 µm in order for nano-network 24 to be more insulated by the bottom insulating layer 23 to be formed subsequently and to maintain the aspect ratio with width. In addition, the mesh size of the nano-network 24 is preferably in the range of 5 nm to 20 µm in view of the process limitation and the structural stability of the nano-network 24, and the structure thereof is not specifically limited, but may include a structure in which shapes, including hexagonal shapes, circular shapes, square shapes and straight line shapes, are repeated.

Next, step (S320) of forming a bottom insulating layer is performed in which the bottom insulating layer 23 is formed in the portion between the sidewalls of the nano-network 24, which excludes the active region, in order to insulate between the active region and the bulk silicon substrate 21. Step (S320) will now be described with reference to FIGS. 5A and 5B.

A dielectric material for forming the bottom insulating layer 23 is not specifically limited, but a silicon oxide or silicon nitride layer capable of effectively blocking leakage current may be deposited as the bottom insulating layer 23. Preferably, the bottom insulating layer 23 is formed of a silicon oxide layer in view of compatibility with a subsequent process and the characteristics of the interface with the silicon substrate. The height of the bottom insulating layer 23 is not specifically limited, but is preferably in the range from 40 nm to 800 nm for effective insulation between the bulk silicon substrate 21 and the nano-network 24. In addition, the height of the nano-network 24 which is exposed to the surface of the bottom insulating layer 23 is also not specifically limited, but is preferably in the range from 10 nm to 200 nm. The bottom insulating layer 23 may be deposited by any one of plasma vapor deposition, chemical vapor deposition and high-density plasma vapor deposition.

Next, step (S330) of implanting impurity ions is performed in which impurity ions are implanted into the source electrode region 22S and the drain electrode region 22D. Step (S330) will now be described with reference to FIGS. 6A and 6B.

In order to increase electrical conductivity, impurity ions are implanted into the source electrode region 22S and the drain electrode region 22D, excluding the region of the nano-network 24. The impurity ions that are implanted may be a material capable of forming a p-type n-type semiconductor. Also, the impurity ions are preferably implanted at a high concentration so that an ohmic contact can be formed between the metal electrode layer 25 and each of the source electrode region 22S and the drain electrode region 22D. Herein, in order to prevent impurity ions from being implanted into the region of the nano-network 24, an impurity implantation preventing layer 24-3 made of a sensitizer or a silicon oxide or silicon nitride layer is patterned on the region of the nano-network 24 by a lithography process and an etching process. Therefore, high-temperature heat treatment is performed to activate the implanted impurity ions.

Next, step (S340) of isolating pins is performed in which a surface damaged by a plasma etching process is removed and the nano-network 24 is completely isolated from the bulk silicon substrate 21. Step (S340) will now be described in detail with reference to FIGS. 7A to 7C.

A surface damaged by a plasma etching process is removed through a thermal oxidation process, and the nano-network 24 is completely insulated from the bulk silicon substrate 21. Herein, in order to protect the portion excluding the region of the nano-network 24, a silicon nitride layer 23-1 is applied to the surface of the nanowire field-effect sensor, and then a patterning process of exposing only the region of the nano-network 24 by a lithography process and an etching process. Then, a damaged surface is removed through a thermal oxidation process, and at the same time, a process of completely isolating pins 24-1 from the bulk silicon substrate 21 by oxidizing the bulk silicon substrate 21 formed below the pins 24-1 vertically arranged on each sidewall is performed.

This pin isolation step (S340) is a step that is performed to more effectively insulate the pins 24-1 from the bulk silicon substrate 21, and may be omitted in view of costs and process complexity.

Next, step (S350) of forming a gate insulating layer is performed in which a gate insulating layer 24-2 is formed on the surface of the nano-network 24 in the nanowire field-effect sensor. Step (S350) will now be described with reference to FIGS. 8A to 8C.

To control the gate of the nanowire field-effect sensor, a gate insulating layer 24-2 is formed on the surface of the pins 24-1 of the nano-network 24 using at least one dielectric material selected from among silicon oxide, silicon nitride, hafnium oxide and aluminum oxide. The formed gate insulating layer 24-2 electrically insulates a fluid from the nano-network 24 to thereby prevent the loss of sensitivity of the nanowire field-effect sensor. In addition, a chemical group capable of fixing a detector material during fabrication of the nanowire field-effect sensor is present on the surface of the gate insulating layer 24-2.

Through step (S350) of forming the gate insulating layer, the process of fabricating the nano-network 24 is completed. Herein, the nano-network 24 has a network structure in which each of the pins 24-1 is vertically arranged on each sidewall of the network and the gate insulating layer 24-2 is applied to the pins 24-1. As used herein, the term "network structure" means a structure in which shapes such as a circular shape and polygonal shapes (including hexagonal shapes) are continuously arranged in all directions. This embodiment illustrates that the nano-network 24 has a structure in which hexagonal structures, that is, hexagonal lattice structures, are continuously arranged in all directions. The structure of the pins 24-1 is not specifically limited, but may include various structures such as cylindrical structures or polygonal structures (including rectangular structures).

Next, step (S360) of forming electrodes are performed in which an electrode metal layer 25 is formed in the source electrode region 22S and the drain electrode region 22D and a submerged gate electrode 29 for applying a gate potential is formed on the bulk silicon substrate 21. Step (S360) will now be described with reference to FIGS. 9A and 9B.

An electrode metal layer 25 is formed on each of the source electrode region 22S and the drain electrode region 22D. In addition, in order to apply a gate potential to the nano-network 24, a submerged gate electrode 29 is formed on a portion of the bottom insulating layer 23, which is near the nano-network 24. In this step of forming this gate electrode, a gate insulating layer unintentionally formed on the source electrode region 22S and the drain electrode region 22D, excluding the nano-network 24, is removed by wet etching before formation of the electrode metal layer 25.

Next, step (S370) of forming a top insulating layer is performed in which a top insulating layer 26 is formed in order to prevent a current from leaking from the source electrode region 22S and the drain electrode region 22D through an electrolyte. Step (S370) will now be described with reference to FIGS. 10A and 10B.

The top insulating layer 26 is formed on the metal layer 25 in order to prevent a current from leaking from the source electrode region 22S and the drain electrode region 22D through an electrolyte. The top insulating layer 26 may be formed of a sensitizer or a dielectric material such as oxide. Herein, the region of the nano-network 24, which is the detector portion of the nanowire field-effect sensor, and the region of the submerged gate electrode 29, are patterned using a lithography process or an etching process so that they can be exposed to a solution.

Next, step (S380) of forming a fluid inlet is performed in which a fluid channel layer is formed in order to transfer a fluid to the nano-network 24 and the submerged gate electrode 29. Step (S380) will now be described with reference to FIGS. 11A and 11B.

In order to transfer a fluid to the region of the submerged gate electrode 29 to operate the nanowire field-effect sensor and transfer a fluid containing the target material 28B to the nano-network 24 which is the detector portion, a fluid inlet is formed. For this purpose, the top insulating layer 27 is formed on the top insulating layer 26, and then a lithography process for patterning the fluid inlet is performed.

Next, as a final step, step (S390) of fixing a detector material is performed in which a detector material 28A that selectively reacts with the target material 28B in the nanowire field-effect sensor is fixed to the surface of the nano-network 24. Step (S390) will now be described with reference to FIGS. 12A and 12B.

The detector material 28A that selectively reacts with the target material 28B is fixed to the surface of the gate insulating layer (24-2), formed on the nano-network 24 in step (S350) of forming the gate insulating layer, through a series of chemical reactions. Thereafter, a fluid containing the target material 28B is injected through the top fluid channel layer 27 so that the target material 28B will react with the detector material 28A. At this time, the electrical conductivity of the nano-network 24 will be changed by the charge of the target material 28B.

The nano-network 24 described above with reference to FIG. 4A to FIG. 8B is not a completed nano-network, but is a nano-network pattern, and a substantial nano-network is the nano-network 24 described above with respect to FIG. 8C to FIG. 12B.

As described above, according to the present invention, the bulk silicon substrate is used instead of the SOI substrate, and thus the fabrication cost of the nanowire field-effect sensor can be greatly reduced. In addition, the nanowire field-effect sensor can be received in a substrate such as a signal processing logic circuit that is fabricated in the bulk silicon substrate, and thus the integration density of the nanowire field-effect sensor is increased.

Moreover, in the fabrication of the nanowire field-effect sensor according to the present invention, the bottom insulating layer is formed below the nano-network pins, and then the pins are isolated from the substrate through an oxidation process. Accordingly, insulation between the pins and the substrate and insulation between the pins are possible, and thus deterioration the sensitivity of the sensor is prevented.

In addition, in the fabrication of the nanowire field-effect sensor according to the present invention, the nano-network having a network structure is formed by vertically arranging the pin on each sidewall of the network and applying the gate insulating layer to the pin. Thus, the detection area of the sensor can be increased to increase the sensitivity of the sensor, and the structural stability of the sensor can be ensured to prevent the characteristics of the sensor element from deteriorating.

Although the preferred embodiments of the present invention have been described for illustrative purposes, those skilled in the art will appreciate that various modifications, additions and substitutions are possible, without departing from the scope and spirit of the invention as disclosed in the accompanying claims.

What is claimed is:

1. A method for fabricating a nanowire field-effect sensor comprising nanowires having a network structure, the method comprising the steps of:
   (a) forming on a bulk silicon substrate an active region, which includes a nano-network, a source electrode region and a drain electrode region, by a lithography process and an etching process;
   (b) forming a bottom insulating layer for insulating between the active region and the bulk silicon substrate, in a region between sidewalls of the nano-network, which excludes the active region, in such a manner that a bottom portion of each of the source electrode region and the drain electrode region is maintained connected to the bulk silicon substrate and a bottom portion of the nano-network is completely insulated from the bulk silicon substrate;
   (c) implanting impurity ions into the source electrode region and the drain electrode region in order to increase an electrical conductivity of the source electrode region and the drain electrode region;
   (d) forming a gate insulating layer on a pin vertically arranged on each sidewall of the nano-network in order to control a gate of the nanowire field-effect sensor;
   (e) forming an electrode metal layer on the source electrode region and the drain electrode region, and forming a submerged gate electrode on the bulk silicon substrate in order to apply a gate potential to the nano-network;
   (f) forming a top insulating layer on the electrode metal layer in order to prevent a current from leaking from the source electrode region and the drain electrode region through an electrolyte;
   (g) forming a fluid inlet by forming a fluid channel layer for transferring a fluid to the nano-network and the submerged gate electrode; and
   (h) fixing a detector material, which selectively reacts with a target material, to a surface of the nano-network.

2. The method of claim 1, further comprising a step of isolating the pin by removing a surface, damaged by a plasma etching process, through a thermal oxidation process, and insulating the nano-network from bulk silicon substrate.

3. The method of claim 1, wherein step (a) of forming the active region comprises a step of patterning the nano-network by any one of electron beam lithography, stepper lithography and scanner lithography, and then subjecting the nano-network to a dry etching or wet etching process.

4. The method of claim 1, wherein step (b) of forming the bottom insulating layer comprises a step of depositing the bottom insulating layer by any one technique selected from among plasma vapor deposition, chemical vapor deposition and high-density plasma vapor deposition, and depositing a silicon oxide or silicon nitride layer.

5. The method of claim 1, wherein step (c) of implanting the impurity ions comprises a step of implanting the impurity ions into the source electrode region and the drain electrode region, which exclude the region of the nano-network, in order to increase the electrical conductivity.

6. The method of claim 1, wherein step (c) of implanting the impurity ions comprises a step of implanting a high concentration of the impurity ions so as to form an ohmic contact between the metal electrode layer and each of the source electrode region and the drain electrode region.

7. The method of claim 1, wherein step (c) of implanting the impurity ions comprises the steps of:
   patterning an impurity implantation preventing layer made of a sensitizer or a silicon oxide or silicon nitride layer on the region of the nano-network by a lithography process and an etching process in order to prevent impurity ions from being implanted into the region of the nano-network; and
   performing high-temperature heat treatment to activate the implanted impurity ions.

8. The method of claim 1, wherein the top insulating layer is formed of a sensitizer or an oxide layer.

9. The method of claim 1, wherein step (f) of forming the top insulating layer comprises a step of patterning the region of the nano-network, which is a detector region of the nanowire field-effect sensor, and the region of the submerged gate electrode, by a lithography process or an etching process, so that the region of the nano-network and the region of the submerged gate electrode are able to be exposed to a solution.

10. The method of claim 1, wherein the nano-network has a structure based on a hexagonal lattice structure.

* * * * *